US005635176A

United States Patent [19]
Samaritani et al.

[11] Patent Number: 5,635,176
[45] Date of Patent: Jun. 3, 1997

[54] PHARMACEUTICAL COMPOSITIONS CONTAINING IL-6

[75] Inventors: Fabrizio Samaritani; Filippo Rendina, both of Rome, Italy

[73] Assignee: Applied Research Systems Ars Holding N.V., Netherlands

[21] Appl. No.: 335,874

[22] PCT Filed: May 7, 1993

[86] PCT No.: PCT/EP93/01120

§ 371 Date: Nov. 10, 1994

§ 102(e) Date: Nov. 10, 1994

[87] PCT Pub. No.: WO93/23065

PCT Pub. Date: Nov. 25, 1993

[30] Foreign Application Priority Data

May 11, 1992 [IT] Italy ................ RM92A0349

[51] Int. Cl.[6] .................................................... A61K 45/05
[52] U.S. Cl. ............................................ 424/85.2; 424/85.1
[58] Field of Search ................................ 424/85.2, 85.1

[56] References Cited

U.S. PATENT DOCUMENTS

| | | | |
|---|---|---|---|
| 4,762,857 | 8/1988 | Bollin, Jr. et al. | 514/777 |
| 4,904,467 | 2/1990 | Schwintera | 424/85.2 |
| 5,078,997 | 1/1992 | Hora et al. | 424/85.2 |
| 5,104,651 | 4/1992 | Boone et al. | 424/85.1 |
| 5,416,071 | 5/1995 | Igari et al. | 514/8 |

FOREIGN PATENT DOCUMENTS

| | | |
|---|---|---|
| 0220574 | 5/1987 | European Pat. Off. |
| 0378171 | 7/1990 | European Pat. Off. |
| 3027320 | 2/1991 | Japan . |
| 2126588 | 3/1994 | United Kingdom . |
| 9000397 | 1/1990 | WIPO . |
| 9116038 | 10/1991 | WIPO . |
| 9306840 | 4/1993 | WIPO . |

OTHER PUBLICATIONS

Paul, "Fundamental Immunol.", Sec. Edn., Raven Press, p. 400, 1989.
Gearing A. H. et al., Lymphobine Res., vol. 5, Suppl. 1, pp. 519–521, 1986.
Manning et al., Pharm. Res., vol. 6 (11), pp. 903–918, 1989.
Wang et al., J. Parental Sci & Tech., vol. 42, No. 25, Supplement, pp. 53–526, 1988.
Hora et al., Lyophilized Formulations of Recombinant Tumor Necrosis Factor., Pharm. Res., Jan. 1992, 9(1) pp. 33–36.
"Freeze–drying of proteins" M. J. Pikal, Biopharm—vol. 3, No. 9, Oct. 1990, pp. 26–30.

*Primary Examiner*—Chhaya D. Sayala
*Attorney, Agent, or Firm*—Ostrolenk, Faber, Gerb & Soffen, LLP

[57] ABSTRACT

Pharmaceutical compositions based on Interleukin-6 (IL-6) stabilized with non reducing sugars, such as sucrose and trehalose. The compositions may also contain an amino acid or human albumin as an excipient. The formulation is particularly suitable for the stabilization of recombinant IL-6 freeze-dried powder.

17 Claims, No Drawings

PHARMACEUTICAL COMPOSITIONS CONTAINING IL-6

The present invention contemplates pharmaceutical compositions containing Interleukin-6 (IL-6), and particularly contemplates compositions based on IL-6 stabilized with nonreducing sugars. Interleukin-6 is a protein belonging to the group of cytokines, which proved to play a key role in the organism immune response and haematopoiesis stimulation (International Symposium on IL-6: Physiopathology and Clinical Potentials, Montreux, Oct. 21–23, 1991).

The prospective therapeutic applications of IL-6 are tumoral growth inhibition, treatment of thrombocytopenia caused by chemotherapy, radiotherapy, and even accidental exposure to radiations. It may also be used as a vaccine adjuvant.

According to the present invention, IL-6 may be either natural or synthetic, i.e. produced on the basis of recombinant DNA technology, the latter being preferred.

The protein of this invention is glycosylated human IL-6, prepared on the basis of the recombinant DNA technology by expression in CHO (Chinese Hamster Ovary) cells, transformed with the corresponding DNA, according to the disclosures of European Patent Application EP 0220574.

As known, purified proteins show a great tendency to become denaturated, even by normal atmospheric agents. This characteristic is even more evident in proteins produced on the basis of recombinant DNA technology. To prevent any contamination of non-human origin, they must be purified to a high degree, which makes their stability lower than that of corresponding purified natural proteins.

IL-6 formulations for injection are obtained on the basis of a process inclusive of freeze-drying for dry powder production.

As described by M. J. Pikal in Biopharm., Oct. 25–30, 1990, the protein pharmacological activity is reduced by phenomena taking place during freeze-drying.

For example, proteic aggregates, which are generally regarded as directly responsible for the onset of allergic manifestations, frequently form during the process. Furthermore, should the protein be not damaged by the various process stresses, a partial denaturation of same during storage operations would be extremely probable.

It is just because of the very easy denaturation of highly purified proteins that it is highly desirable to produce stable formulations with an as long life cycle as possible, even when stored at ambient temperature.

The expression "formulation stability" is used to mean that the protein maintains its activity both during the pharmaceutical preparation and storage.

The formulations containing highly purified proteins may be stabilized by addition of one or more excipients preventing or delaying the active ingredient degradation.

Excipients of different chemical nature were used in various proteins formulations.

High molecular weight stabilizers of biological origin, such as sea colloids, dextran, and phospholipids, are known.

Equally effective stabilizers often proved to be the formulations containing proteins, e.g. albumin, amino acids, e.g. arginine or glycine, and sugars, e.g. monosaccharides or oligosaccharides. Another cytokine, i.e. Interleukin-2 (IL-2), and particularly its recombinant form, was formulated with various stabilizers, preferably albumin and amino acids.

International patent application WO 90/00397 discloses IL-2 stabilization with arginine or carnitine or a mixture thereof, with betaine, pyridoxine, polyvinylpyrrolidone, carboxylic acids salts, and by the addition, if any, of other excipients, such as sugars and citrate buffer.

European patent application EP 158487 discloses IL-2 formulations with human albumin and a reducing compound, such as glutathione, N-acetylcysteine or ascorbic acid.

Pikal in Biopharm., Oct. 25–30, 1990, also suggests that excipients capable of bringing about amorphous and/or vitreous structures can cause protein stabilization on drying.

The amorphous structure seems to secure a considerable restriction of protein molecular mobility, with consequent decrease in chemical reactivity, as well as a long lasting protection: in fact, it is supposed to form a sort of casing where the protein is housed and, therefore, protected also after the process cycle.

However, Pikal states that an amorphous excipient is not sufficient for stability increase. Actually, the protein may be denaturated just by interacting with the amorphous excipient.

The conclusion is that a general criterion for proteins formulation cannot be put forward: the optimal formulation composition can be determined only through an exacting work of screening of a large number of substances.

The study of a new protein, such as IL-6, required an in-depth investigation of various stabilizing agents, including the substances that give an amorphous structure, such as nonreducing sugars.

It has surprisingly been found that nonreducing sugars, such as for example sucrose and trehalose, increase the stability of IL-6 formulation.

It is the main object of the present invention to provide a pharmaceutical composition containing an intimate mixture of IL-6 and a stabilizing quantity of a nonreducing sugar either alone or in conjunction with other excipients.

It is a further object of the present invention to provide a procedure for the preparation of said pharmaceutical composition, including the components for aqueous solution freeze-drying.

It is a further object of the present invention to provide a form of said pharmaceutical composition in which the aforesaid intimate solid mixture is hermetically enclosed in a sterile container suitable for storage before use and for the mixture reconstitution in a solution for injection.

It is a further object of the present invention to provide a solution of said solid mixture reconstituted in a solution for injection.

With a view to evaluating the excipient effect on the active ingredient stability, several formulations of recombinant IL-6 containing 35 µg/vial were prepared with various excipients, such as mannitol, sucrose, trehalose, lactose mixed with an amino acid, such as arginine or glycine, or with human serum albumin (HSA). Table 1 shows the composition of the various formulations prepared (A1, A2, A3, A4, etc.), expressed as content (in mg) per vial. All formulations contain arginine or glycine or human serum albumin (HSA) in addition to other excipients.

TABLE 1

| COMP. FORM. | HSA mg | Mannitol mg | Saccharose mg | Trehalose mg | Lactose mg | Arginine HCl mg | Glycine mg | $Na_2HPO_4$ | $Na_2HPO_4$ |
|---|---|---|---|---|---|---|---|---|---|
| A1 | 0.2 | 25 | | | | 0.125 | | 0.313 | 0.336 |
| A2 | 0.2 | 25 | | | | | 0.5 | 0.313 | 0.336 |
| A3 | 0.2 | | 47.5 | | | 0.125 | | 0.313 | 0.336 |
| A4 | | 25 | | | | 0.125 | | 0.313 | 0.336 |
| A5 | | | 47.5 | | | 0.125 | | 0.313 | 0.336 |
| A6 | | | | 47.5 | | 0.125 | | 0.313 | 0.336 |
| A7 | | 23.7 | | | | 1.5 | | 0.313 | 0.336 |
| A8 | | | 44.5 | | | 1.5 | | 0.313 | 0.336 |
| A9 | | | | | 44.5 | 1.5 | | 0.313 | 0.336 |
| A10 | | | | | | 1.5 | 10.4 | 0.313 | 0.336 |

Formulations of recombinant IL-6 (35 µg) (content/vial)

The freeze-dried powder was obtained on the basis of the following process: IL-6 bulk was diluted with the excipient solution in phosphate buffer at pH 7. The solution obtained was filtered, made up to volume, poured into the vials, and freeze-dried.

The samples were maintained at 50° C. and subjected to immunologic- and bioassays at set time intervals.

The immunologic assay was carried out using QUAN-TIKINE kit, (R&D SYSTEMS Inc.), cat. No. D6050, following the instructions attached thereto.

The bioassay was carried out as described by Normann and Potter in Science, 233, 566–569, 1980. The assay measures IL-6 activity by exploiting IL-6 capability of acting as a growth factor of a particular cell line (plasmacytoma T-1165).

Activity is expressed in international units/solution milliliter (IU/ml).

An international unit is the quantity of IL-6 producing 50% of maximum cell growth.

In this specification, the measure is expressed as per cent recovery of the activity of sample IL-6 in the various formulations, on the assumption that the sample activity at zero time is 100%. Assays were carried out in duplicate.

Tables 2 and 3 show the results of assays conducted on the samples of Table 1 after 4, 5, 7, 8 and 9 weeks (Table 2) and after 10, 12, and 21 weeks (Table 3).

Samples A1 to A6 were subjected to immunologic assay (Table 2) and samples A7 to A10 were subjected to bioassay (Table 3).

TABLE 2

Stability at 50° C. of IL-6 formulations A1 to A6 (35 µg) by immunologic assay, expressed as % recovery vs. zero time

| Formulation | 50° C. | | | | |
|---|---|---|---|---|---|
| | 4W | 5W | 7W | 8W | 9W |
| A1 | | | 62 | 80 | 84 |
| A2 | | | 78 | 80 | 80 |
| A3 | | | 103 | 120 | 112 |
| A4 | 81 | 82 | | | |
| A5 | 107 | 104 | | | |
| A6 | 89 | 100 | | | |

W = weeks

TABLE 3

Stability at 50° C. of IL-6 formulations A7 to A10 (35 µg) by bioassay, expressed as % recovery vs. zero time

| Formulation | 50° C. | | |
|---|---|---|---|
| | 10W | 12W | 21W |
| A7 | 38 | 35 | 37 |
| A8 | 104 | 95 | 74 |
| A9 | 51 | 49 | |
| A10 | 56 | 61 | |

W = weeks

The data shown in the Tables reported above demonstrate that the compositions containing nonreducing sugar, such as e.g. sucrose or trehalose, (A3, A5, A6, A8) are much more stable than the compositions containing mannitel or lactose (A1, A2, A4, A6, A7). With a view to evaluating the effect of arginine, glycine or albumin on the formulations stability, IL-6 compositions containing sucrose of lactose alone vs. compositions containing the additional excipient were prepared (Table 4).

For the purpose of evaluating the effect of pH on the stabilizing action of the various components, the formulations were prepared by freeze-drying aqueous solutions at various pH (5.5, 6, and 7).

TABLE 4

Recombinant IL-6 formulations (35 μg) containing sucrose or lactose with or without additional excipient (content/vial)

| Comp. Form. | Saccharose mg | Lactose mg | Arginine HCl mg | HSA mg | Na$_2$HPO$_4$ mg | NaH$_2$PO$_4$ mg | pH |
|---|---|---|---|---|---|---|---|
| B1 | 45 | | | | 0.035 | 1.17 | 5.5 |
| B2 | | 45 | | | 0.035 | 1.17 | 5.5 |
| B3 | 40.4 | | 1.5 | | 0.035 | 1.17 | 5.5 |
| B4 | | 40.4 | 1.5 | | 0.035 | 1.17 | 5.5 |
| B5 | 45 | | | 0.25 | 0.035 | 1.17 | 5.5 |
| B6 | 45 | | | | 0.107 | 1.11 | 6.0 |
| B7 | | 45 | | | 0.107 | 1.11 | 6.0 |
| B8 | 40 | | 1.5 | | 0.107 | 1.11 | 6.0 |
| B9 | | 40 | 1.5 | | 0.107 | 1.11 | 6.0 |
| B10 | 45 | | | 0.25 | 0.107 | 1.11 | 6.0 |
| B11 | 48 | | | | 0.313 | 0.336 | 7.0 |
| B12 | | 48 | | | 0.313 | 0.336 | 7.0 |
| B13 | 43.3 | | 1.5 | | 0.313 | 0.336 | 7.0 |
| B14 | | 43.3 | 1.5 | | 0.313 | 0.336 | 7.0 |
| B15 | 48 | | | 0.25 | 0.313 | 0.336 | 7.0 |

The stability of the above formulations was studied on samples maintained at 25° C. and 50° C.; the residual activity was measured at the time intervals shown in Tables 5 and 6. Table 5 illustrates the stability data of samples subjected to immunologic assay and Table 6 shows the stability data of samples subjected to bioassay. Activity data are expressed as % recovery vs. zero time.

TABLE 5

Comparison among stability data of IL-6 formulations (35 μg) containing sucrose or lactose with or without an additional excipient. (% recovery vs. zero time) - immunologic assay

| | 25° C. | | | | | | | | 50° C. | | | | | | |
|---|---|---|---|---|---|---|---|---|---|---|---|---|---|---|---|
| Form. | 2W | 3W | 4W | 6W | 7W | 8W | 9W | 10W | 2W | 3W | 4W | 6W | 7W | 8W | 10W |
| B1 | 98 | | | 112 | | | | | 112 | | | 103 | | | |
| B2 | | 92 | | | | | | | 99 | | | 89 | | | |
| B3 | 86 | | | 96 | | | | | 129 | | | | | | |
| B4 | 90 | | | | | | | | 91 | | | 72 | | | |
| B5 | 91 | | | 86 | | | | | 89 | | | 83 | | | |
| B6 | | | 112 | | | | | | | | 104 | | 101 | | |
| B7 | | | 89 | | 74 | | | | | | 71 | | | | |
| B8 | | | 115 | | 93 | | | | | | 112 | | 107 | | |
| B9 | | | 97 | | 90 | | | | | | 97 | | 110 | | |
| B10 | 88 | | | 85 | | | | | | 95 | | | | | |
| B11 | | | 91 | 116 | 98 | | 119 | | | | 95 | | 120 | | 101 |
| B12 | | | 105 | | | | 95 | | | | 103 | | | | 87 |
| B13 | | | 107 | | 102 | | 100 | | | | 87 | | | 80 | |
| B14 | | | 103 | | 86 | | 92 | | | | 94 | 119 | | | |
| B15 | | 107 | | | 11 | 103 | | | | 105 | | | | | |

W = weeks

TABLE 6

Comparison among stability data of IL-6 formulations (35 μg) containing sucrose or lactose with or without an additional excipient. (% recovery vs. zero time) - bioassay

| | 25° C. | | | | | | | | 50° C. | | | | | | |
|---|---|---|---|---|---|---|---|---|---|---|---|---|---|---|---|
| Form. | 2W | 3W | 4W | 5W | 6W | 7W | 8W | 9W | 2W | 3W | 4W | 5W | 6W | 7W | 8W | 9W |
| B1 | 107 | | | | 96 | | 100 | | 93 | | 105 | | | | 91 | |
| B2 | 109 | | | | 94 | | 86 | | 99 | | 85 | | | | 75 | |
| B3 | 117 | | | | 98 | | | | 105 | | 93 | | 103 | | | |
| B4 | 90 | | 103 | | | | 96 | | 104 | | 94 | | | | 77 | |
| B5 | 94 | | 103 | | | | 81 | | 100 | | 98 | | | | 93 | |
| B6 | 92 | | | 96 | 108 | | | | 96 | 106 | | | | 95 | | 103 |
| B7 | 110 | | | | 84 | | | | 104 | | | 83 | | 70 | | |
| B8 | 113 | | | 109 | 103 | | | 120 | 118 | 119 | | | 106 | | | 118 |

TABLE 6-continued

Comparison among stability data of IL-6 formulations (35 μg) containing sucrose or lactose with or without an additional excipient. (% recovery vs. zero time) - bioassay

| | 25° C. | | | | | | | | 50° C. | | | | | | | |
|---|---|---|---|---|---|---|---|---|---|---|---|---|---|---|---|---|
| Form. | 2W | 3W | 4W | 5W | 6W | 7W | 8W | 9W | 2W | 3W | 4W | 5W | 6W | 7W | 8W | 9W |
| B9 | 93 | | | 72 | | | | | 80 | 75 | | 68 | | | | |
| B10 | 106 | | | | | 109 | | | 103 | | 92 | | | | 112 | |
| B11 | | 106 | | 98 | | | | 111 | 115 | | | 113 | | | | 104 |
| B12 | | 110 | | 81 | | | | 102 | 81 | | | 74 | | | | 70 |
| B13 | | 94 | | | | 97 | | | 88 | | | | 95 | | | |
| B14 | | 94 | | | 103 | | | | 95 | | | 70 | | 73 | | 69 |
| B15 | 97 | | | | | 110 | | | | | 89 | | | | 102 | |

W = weeks

As may be seen, the further excipients, i.e. arginine and albumin, added to the formulations containing sucrose and lactose participate in the stabilizing action to a negligible extent.

Stability was measured by bioassay, still expressed as percent activity recovery at zero time.

TABLE 8

Study of the stability of IL-6 plus sucrose formulations. Percent recovery vs. zero time - Immunologic assay

| | 25° C. | | | | 37° C. | | | | 50° C. | | | |
|---|---|---|---|---|---|---|---|---|---|---|---|---|
| Form. | 2W | 4W | 8W | 10W | 2W | 4W | 8W | 10W | 2W | 4W | 8W | 10W |
| C1 | 105 | 90 | 94 | 97 | 111 | | 94 | | 101 | 95 | | 90 |
| C2 | | 94 | 102 | | | 97 | 105 | | | | 105 | 98 |

W = weeks

The data listed in Tables 5 and 6 also demonstrate that the formulations containing a nonreducing sugar, e.g. sucrose, show a much lower denaturation than those containing a reducing sugar, such as lactose.

Formulations at pH 7 and those at pH 5.5 or 6 show an analogous denaturation: it follows that, in the range considered, the influence of pH value on the formulation stability seems negligible. In any case, pH values approaching or equalling neutrality are preferred for the formulations for injection.

The formulation selected for an in-depth study contains sucrose, at pH 7. For the purpose of evaluating dosage influence on stability, two compositions containing different quantities of active ingredients were prepared (Table 7).

TABLE 7

Formulations of recombinant IL-6 with sucrose (content/vial)

| Comp. Form. | Saccharose mg | Na$_2$HPO$_4$/NaH$_2$PO$_4$ mg | pH | IL-6 mg |
|---|---|---|---|---|
| C1 | 48 | 0.313  0.336 | 7 | 0.035 |
| C2 | 48 | 0.313  0.336 | 7 | 0.350 |

The investigation was carried out on samples stored in vials for 2, 4, 8, and 10 weeks at 25° C., 37° C., and 50° C. Stability was measured by immunologic assay expressed as per cent recovery of the sample activity at zero time (Table 8).

Table 9 recapitulates the stability of samples stored in vials for 4, 10, and 12 weeks at the aforesaid temperatures.

TABLE 9

Study of the stability of IL-6 plus sucrose formulations. Percent recovery vs. zero time - Bioassay

| | 25° C. | | | 37° C. | | | 50° C. | | |
|---|---|---|---|---|---|---|---|---|---|
| Form. | 4W | 10W | 12W | 4W | 10W | 12W | 4W | 10W | 12W |
| C1 | 91 | 100 | 92 | 80 | 90 | | 92 | 96 | 94 |
| C2 | 113 | | | 107 | | | 95 | | |

W = weeks

As shown from the data of Tables 8 and 9, the denaturation of the formulations containing sucrose is extremely low and different IL-6 dosages do not affect the formulation stability.

The very low denaturation of the aforesaid compositions was confirmed by chromatographic analyses conducted on samples at the same time intervals and at the same temperatures as mentioned above. Chromatographic analysis by molecular size separation was carried out with VARIAN MICROPAK TSK GEL G-3000 SW column (diameter: 7.5 mm, length: 30 cm) at a flow rate of of 0.4 ml/min. The mobile phase was a 100 mM phosphate buffer at pH 6.85 and 11.69 g/l NaCl.

The analyses did not show any variation of the samples chromatographic profile in respect of zero time and confirmed that sucrose was the most appropriate excipient for IL-6 formulations stabilization.

EXAMPLES OF PHARMACEUTICAL PRODUCTS

Materials: extra pure sucrose Ph fur, BP, Ph Nord, NF (Merck); reagent grade $Na_2HPO_4.2H_2O$ (Merck), $NaH_2PO_4.H_2O$ (Merck); 0.1 M phosphoric acid (Merck); 0.1 M NaOH (Merck); water for injection. The containers used were DIN 2R glass vials (borosilicate glass, type I) sealed with Pharmagummi butyl rubber and aluminium ring. Preparation of IL-6 solution containing sucrose (for 1000 vials containing 35 µg IL-6/vial)

Saccharose (48 g), $Na_2HPO_4.2H_2O$ (0.313 g) and $NaH_2PO_4.H_2O$ (0.336 g) were dissolved in water For injection (400 ml) to form the initial sucrose solution. The obtained solution was divided into two equal parts. Recombinant IL-6 bulk (35 mg) was diluted with one solution part and adjusted to pH 7 with 0.1 M NaOH or $H_3PO_4$. The two solutions were diluted to the final volume of 250 ml with water for injection.

The solution containing IL-6 was filtered through a 0.22µ Durapore sterile filter and diluted to the final volume with the remaining excipients solution, filtered through the same Durapore filter. During the process, the solution temperature was maintained at 4° C. to 8° C.

IL-6 solutions containing other excipients or a different quantity of active ingredient were prepared Following an analogous procedure.

Filling and freeze-drying

Vials were filled with 0.5 ml IL-6 solution, placed in the freeze-drier, and cooled to −45° C. for 3 to 6 hours. Freeze-drying started at −45° C. under 0.07 millibar vacuum. Heating scheme was as follows: +10° C. for 10 to 12 hrs, then +30° C. until the cycle end.

The reconstituted solution was subjected to the usual quality controls.

Although the present invention has been illustrated by specific examples, it is understood that variations to the applications described herein can be introduced without falling outside the spirit and object thereof.

We claim:

1. A pharmaceutical composition containing an intimate solid mixture of Interleukin-6 (IL-6) and a stabilizing quantity of a nonreducing sugar as stabilizing agent either alone or in conjuction with excipients, said intimate solid mixture being a freeze-dried powder.

2. The pharmaceutical composition according to claim 1 wherein said nonreducing sugar is sucrose or trehalose.

3. The pharmaceutical composition according to claim 1, wherein said IL-6 is recombinant.

4. The pharmaceutical composition according to claim 1, wherein said stabilizing agent consists of sucrose.

5. The pharmaceutical composition according to claim 1, wherein said stabilizing agent is sucrose or trehalose in combination with an amino acid.

6. The pharmaceutical composition according to claim 5 wherein said amino acid is arginine.

7. The pharmaceutical composition according to claim 1, wherein said stabilizing agent is sucrose or trehalose in combination with albumin.

8. The pharmaceutical composition according to claim 1, containing 35 or 350 µg of IL-6 and 48 mg of sucrose.

9. The pharmaceutical composition according to claim 1, containing 35 or 350 µg of IL-6 and 47.5 mg of trehalose.

10. A hermetically closed sterile container containing the pharmaceutical composition according to claim 1.

11. A solution containing the solid mixture according to claim 1 in a solvent for injection.

12. In a process for the preparation of a solid pharmaceutical composition comprising the preparation of an aqueous solution of the components for the composition, distribution of the solution into containers and drying or freeze-drying of the solution in the containers, the improvement wherein the components are a mixture of Interleukin-6 and a stabilizing quantity of a non-reducing sugar.

13. The process according to claim 12, wherein the pH of the solution ranges between 5.5 and 7.0.

14. The process according to claim 13 wherein the pH of the solution is 7.

15. In a process for the preparation of a solid pharmaceutical composition comprising preparing an aqueous solution of the components for the pharmaceutical composition, drying or freeze-drying the aqueous solution and distributing the solid mixture obtained into containers, the improvement wherein the components are a mixture of Interleukin-6 and a stabilizing quantity of a non-reducing sugar.

16. The process according to claim 15, wherein the pH of the solution ranges between 5.5 and 7.0.

17. The process according to claim 16, wherein the pH of the solution is 7.

* * * * *